United States Patent [19]

Kinney et al.

[11] 4,161,952

[45] Jul. 24, 1979

[54] WOUND WIRE CATHETER CARDIOVERTING ELECTRODE

[75] Inventors: Philip C. Kinney, Pittsburgh; Marlin S. Heilman, Gibsonia; Alois A. Langer, Pittsburgh, all of Pa.

[73] Assignee: Mieczyslaw Mirowski, Owings Mills, Md.

[21] Appl. No.: 847,443

[22] Filed: Nov. 1, 1977

[51] Int. Cl.² .............................................. A61N 1/04
[52] U.S. Cl. .................................................. 128/786
[58] Field of Search ..................... 128/404, 418, 419 P, 128/419 D

[56] References Cited

U.S. PATENT DOCUMENTS

| | | | |
|---|---|---|---|
| 3,348,548 | 10/1967 | Chardack | 128/418 |
| 3,416,533 | 12/1968 | Fisher et al. | 128/404 |
| 3,474,791 | 10/1969 | Bentov | 128/419 P |
| 3,533,403 | 10/1970 | Woodson | 128/419 P |
| 3,664,347 | 5/1972 | Harmjanz | 128/404 |
| 3,788,329 | 1/1974 | Friedman | 128/418 |
| 3,804,098 | 4/1974 | Friedman | 128/419 P |
| 3,815,611 | 6/1974 | Denniston | 128/419 D |
| 3,857,398 | 12/1974 | Rubin | 128/419 D |
| 3,903,896 | 9/1975 | Harmjanz | 128/418 |
| 3,942,536 | 3/1976 | Mirowski et al. | 128/419 D |
| 4,030,509 | 6/1977 | Heilman | 128/419 D |
| 4,033,355 | 7/1977 | Amundson | 128/419 P |

*Primary Examiner*—William E. Kamm
*Attorney, Agent, or Firm*—Fleit & Jacobson

[57] ABSTRACT

Disclosed is an implantable catheter-type cardioverting electrode whose conductive discharge surface is comprised of coils of wound spring wire. An electrically conductive lead extends through the wound wire section of the electrode and has its distal end connected to the discharge coil at two locations. The proximal end of the conductive lead is adapted for connection to an implanted pulse generator. A pliable elastomeric material such as a medical-grade adhesive fills the conductive coils in the wound wire section of the spring wire electrode so that only the outer periphery of the wound section is exposed to the body. The catheter electrode is flexible, allowing easy implantation and avoiding trauma after implantation, and provides a large discharge surface for effecting defibrillation. The electrode is designed to reside in or about the heart, as in the superior vena cava or in the coronary sinus, and acts against another implanted electrode such as a conformal electrode residing at the apex of the heart.

36 Claims, 4 Drawing Figures

WOUND WIRE CATHETER CARDIOVERTING ELECTRODE

BACKGROUND OF THE INVENTION

It is well known that arrhythmias such as ventricular fibrillation, can be reversed by passing high energy electric current through the fibrillating myocardium. This can be accomplished by means of external chest paddles placed on the patient's thorax in a hospital coronary care unit, or by electrodes applied directly to the surface of the heart in open heart surgery. Ventricular defibrillation can also be accomplished by using permanently implanted electrodes.

Already known is a catheter electrode system having two discrete conductive electrodes (or electrode sets) on a single implantable catheter. During defibrillation, an electrical field is established between the two electrodes on the catheter, and defibrillation is effected by depolarizing a critical mass of the myocardium. By so depolarizing this critical mass, the heart is brought back to normal cardiac rhythm. A bipolar catheter electrode is shown in commonly assigned U.S. Pat. No. 3,942,536.

Use of the bipolar catheter electrode reduces the energy requirements associated with external paddle defibrillation. Another effective low-energy approach to defibrillation through implanted electrodes is shown in commonly assigned U.S. Pat. No. 4,030,509. In this patent, defibrillation is accomplished by a conformal apex electrode which acts against, for example, a catheter electrode situated high in the heart or in the superior vena cava.

The bipolar catheter electrode shown in U.S. Pat. No. 3,942,536 comprises an electrically conductive lead molded in a silicone rubber casing wherein each of two electrodes is comprised of a plurality of spaced, conductive low impedance rings. The conductive electrode of the catheter shown in U.S. Pat. No. 4,030,509 is illustrated in a similar manner. This catheter electrode design, which is typical of the state of the art, is adequate. However, there is room for improvement in the design of the defibrillating catheter electrode.

Because of its being permanently implanted in a heart, any catheter electrode, whether bipolar or monopolar, must be capable of withstanding repeated lateral and axial flexing as well as momentary elongation, all over long periods of time. In addition, the electrode must have a relatively large surface area in order to efficiently discharge high amounts of energy for effective defibrillation, and must of course maintain its electrical integrity. The catheter electrode must also be biocompatible, that is, of biocompatible materials, as well as of a configuration having a smooth exterior surface to avoid tissue damage and to avoid the formation of clots. It is the object of the present invention to provide just such an electrode.

SUMMARY OF THE INVENTION

The present invention is generally related to the field of electrical cardioversion, and more specifically to an implantable catheter electrode for accomplishing this result.

"Cardioverting" or "cardioversion" as used herein is intended to encompass the correction of a number of arrhythmic heart conditions, both lethal and non-lethal. Those arrhythmic heart conditions include atrial tachycardia, atrial flutter, atrial fibrillation, junctional rhythms, ventricular tachycardia, ventricular flutter, and ventricular fibrillation, and any other non-pacemaking related arrthyhmic condition which may be corrected by applying electrical shocks to the heart. Obviously then, "defibrillation" is included in the term cardioversion as a method of applying electrical shocks to the heart to defibrillate fibrillating atria or fibrillating ventricles.

The catheter electrode of the present invention includes a resilient wound wire discharge electrode having proximal and distal ends. An electrically conductive lead extends at least partially through the wound wire discharge section of the resilient wire electrode, and is connected to the wound wire discharge section at its distal end. The proximal end of the lead is adapted for connection to a pulse generator. A pliable material fills the wound section of the resilient wire electrode so that only the outer periphery of the wound section is exposed to the body. In this manner, the possibility of tissue damage is decreased; the electrode is sealed from entry of blood; and the possibility of clotting is minimized. The lead is connected to the wound wire discharge electrode both at the proximal and distal ends thereof; and the section of the lead between the proximal and distal ends of the discharge electrode is encased in a protective sheath. The catheter electrode system is formed from biocompatible materials, and is flexible so that it can be safety inserted into position in the heart, and so that it can reside in the heart for long periods of time without trauma to the surrounding tissue. In addition, the resilient wire electrode provides substantial contact surface so as to enable the discharge of energy into the heart to effect cardioversion.

The inventive catheter electrode system is preferably positioned in the superior vena cava or in the coronary sinus, and preferably acts against an apex electrode such as that shown in U.S. Pat. No. 4,030,509.

DETAILED DESCRIPTION OF THE DRAWINGS

Figure 1:
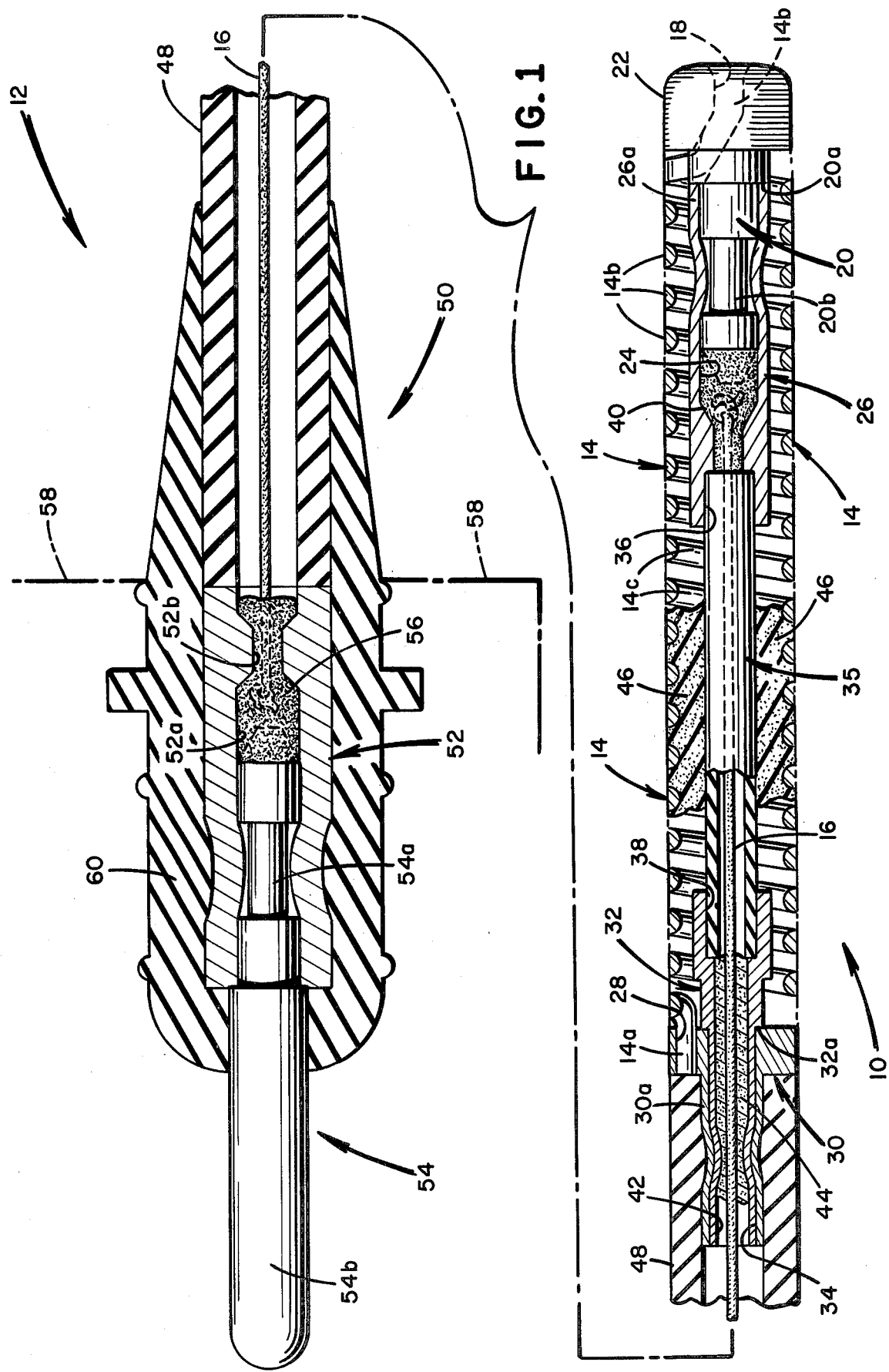
FIG. 1 is a longitudinal section of the catheter electrode system of the present invention.
Figure 2:
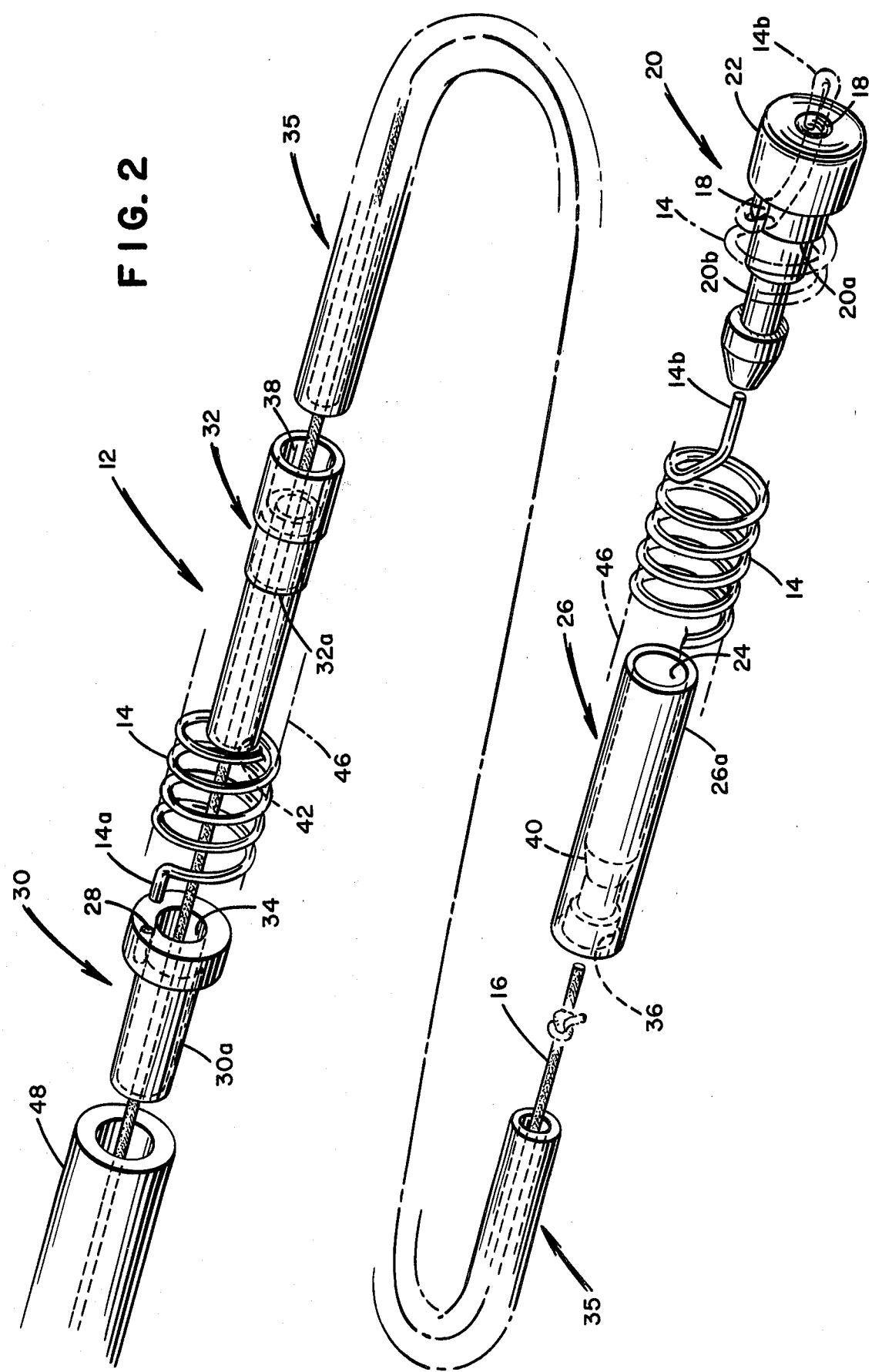
FIG. 2 is an exploded perspective, partially broken away, illustrating the distal end of the catheter electrode system of FIG. 1.

Referring now to FIGS. 1 and 2, the inventive catheter electrode system is shown generally at 12. The distal end 10 of the catheter electrode system 12 comprises an electrically conductive spring wire 14 formed into a helical coil having a proximal end 14a and a distal end 14b. The helical coil is conveniently formed by winding the spring wire 14 on a mandrel; preferably, the turns 14c of the helical coil are spaced apart to provide gaps between the turns prior to final assembly, and the outer peripheral surface 14d of the spring wire 14 is ground and polished for smoothness. The ends 14a and 14b of the spring wire 14 extend longitudinally of the helical coil portion to provide electrical connection points. For illustrative purposes, a titanium spring wire 14 may be used, having a 30 mil diameter and wound on an 0.135 inch mandrel at 20 turns per inch to provide a helical coil with a spacing of 0.050 inch center-to-center between turns, a diameter of 0.165 inch after grinding and polishing, and a length of about 3 inches.

Figure 4:
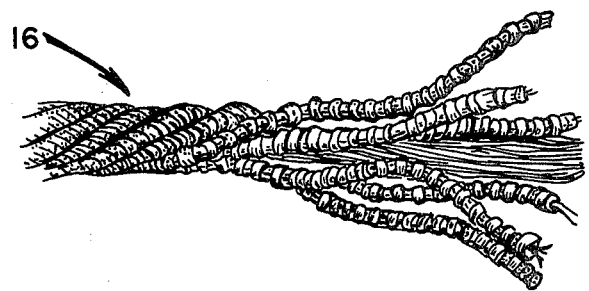
FIG. 4 is a view illustrating the silver tinsel wire used in the inventive electrode system.

An electrically conductive lead 16 extends partially through the helical coil of the spring wire 14 and includes a proximal end and a distal end. The proximal end of the lead 16 is adapted to be connected to an implanted pulse generator, and the distal end of the lead 16 is electrically coupled to the spring wire 14. The lead 16 may, for example, as shown in FIG. 4, be tinsel wire which comprises a central strand of polyester yarn about which is wound a plurality of strands having a polyester yarn core and a ribbon winding. Preferably, for reasons of biocompatability and electrical conductivity, the ribbon is of silver or gold. This lead construction is capable of efficiently conducting the high energies utilized in delivering defibrillating pulses to a heart. Tinsel wire is capable of withstanding virtually indefinite flexions without damage due to the substantial length of ribbon relative to the overall length of the lead 16 itself. Furthermore, the silver or gold ribbon is capable of efficiently delivering the high energy generally required when cardioverting a heart.

The distal end 14b of the spring wire 14 extends through an opening 18 in the distal end of an electrically conductive male plug 20. In assembling the catheter electrode system 12, the distal end 14b of the spring wire 14 is fed through the opening 18 in the male plug 20, is bent over on itself to form a length of, for example, 0.20 inch extending out of the distal end of the male plug 20, and is then plasma welded to the male plug 20. The plasma welding causes the tip of the distal end 14b of the spring wire 14 to melt and fill the opening 18 in the male plug 20 before solidifying. This provides a good physical and electrical connection between the spring wire 14 and the male plug 20. The end 14b of the spring wire 14 is then polished smooth, so as to be flush with the tip of male plug 20, and thus avoid damage to tissue when the catheter electrode system 12 is implanted.

The proximal end of the male plug 20 is received in an opening 24 defined by a sleeve 26a forming the distal end of an electrically conductive female plug 26. The extreme distal end of the female plug 26 abuts against a shoulder 20a defined by the male plug 20. The female plug 26 is smaller in outer diameter than the inner diameter of the helical coil of the spring wire 14 so that a space is defined therebetween. The male plug 20 has a circumferential groove 20b formed around its mid-section and the female plug 26 is crimped at this point so that the female plug 26 is securely retained around the male plug 20 and is in good electrical contact therewith.

The proximal end 14a of the spring wire 14 extends through an opening 28 in the distal end of an electrically conductive female plug 30. The tip of the proximal end 14a of the spring wire 14 is plasma welded in the opening 28 in the female plug 30 in similar manner to that employed in attaching the distal end 14b of the spring wire 14 to the male plug 20. The end 14b is then polished smooth. The female plug 30, which has the same outer diameter as the ground and polished helical coil spring wire 14, extends away from the distal end 10 of the catheter electrode system 12 and defines a sleeve 30a.

The proximal end of an electrically conductive male plug 32 extends through the opening 34 defined by the sleeve 30a of the female plug 30. A shoulder 32a of the male plug 32 abuts against the extreme distal end of the female plug 30. The distal end of the male plug 32 extends partially through the helical coil of the spring wire 14 and faces the extreme distal end 10 of the catheter electrode system 12. The distal end of the male plug 32 is smaller in outer diameter than the inner diameter of the helical coil of the spring wire 14 so that a space is defined therebetween. The female plug 30 is crimped around the proximal end of the male plug 32 to retain the male plug 32 in position and to provide good electrical contact. The male plugs 20 and 32 and female plugs 26 and 30 may, for example, be of titanium.

A protective tube 35 has a distal end inserted into an opening 36 defined by the proximal end of the female plug 26 and is secured therein by medical-grade adhesive. The proximal end of the tube 35 is inserted into an opening 38 defined by the distal end of the male plug 32 and is secured therein by medical-grade adhesive. The tube 35 serves to protect the tinsel wire lead 16 from mechanical abrasion due to flexions of the electrode. As illustrated, the tube 35 is formed from an insulating elastomeric material such as "Silastic" sold by the Dow Corning Corporation. However, the tube could be of an electrically conductive material. The tube 35, like the female plug 26 and distal end of the male plug 32, has a smaller outer diameter than the inner diameter of the helical coil of the spring wire 14.

The extreme distal end of the lead 16 is knotted so that it is retained in the opening 24 defined by the sleeve 26a of the female plug 26 adjacent the proximal end of the male plug 20. This opening 24 is filled with an electrically conductive polymer 40 such as a metal-filled (e.g., with silver) epoxy to provide good electrical connection from the lead 16, through male and female plugs 20 and 26, respectively, to the distal end of the spring wire 14. In like manner, the opening 42 defined by the male plug 32 is filled with an electrically conductive polymer 44. The remaining space defined by the spring wire is filled with a pliable material 46 which maintains its integrity notwithstanding flexions of the catheter and its conductive coil discharge surface. As illustrated, the material 46 is an electrically insulating elastomeric, medical-grade adhesive so that only the outer peripheral surface 14d of the helical coil spring wire 14 is electrically exposed to the body. Filler material 46 can also be conductive, thereby increasing the electrical contact surface of the electrode.

Placement of the filler material 46 can conveniently be accomplished after the catheter electrode system is assembled, by placing a heat shrinkable tube around the helical coil spring wire 14, heating and thereby shrinking the tube, injecting the elastomeric, medical-grade adhesive 46 through an opening in the tube between the turns 14c of the helical coil, removing the heat shrinkable tube, cleaning the outer peripheral surfaces 14d of the helical coil, and finally, filling any voids in the surface of the adhesive 46.

An electrically insulating tube 48, preferably formed from an elastomer such as "Silastic", surrounds the proximal end of the female plug 30 and extends away from the distal end 10 of the catheter electrode system 12. The tube 48 has substantially the same outer diameter as the outer diameter of the ground and polished coil spring wire 14.

Referring now to the proximal end 50 of the catheter electrode system 12, it can be seen that a female plug 52 has its distal end abutting against the proximal end of the insulating tube 48. The proximal end of the female plug 52 defines a sleeve 52a which receives the distal end of a male plug 54 having a circumferentially extending groove 54a. The proximal end of the female plug 52 is crimped around the circumferentially extending groove 54a in the male plug 54. The male and female plugs may, for example, be formed from titanium.

The proximal end of the lead 16 is fed through an opening 52b in the female plug 52, and is knotted so that it is retained in the sleeve 52a defined by the female plug 52 adjacent the distal end of the male plug 54. The space defined by the sleeve 52a surrounding the knotted end of the lead is filled with an electrically conductive polymer 56 such as a metal-filled epoxy to provide a good electrical connection with the male plug 54. The proximal end of the male plug defines a prong 54b for plugging into a pulse generator shown in phantom at 58. Finally, an electrically insulating boot 60 surrounds the distal end of male plug 54, the female plug 52, and a portion of the tube 48. The proximal end of the male plug 54 extends out of boot 60 so that electrical connection can be made to pulse generator 58. The boot is preferably of an elastomer such as "Silastic", and is attached to the female plug 52 and tube 48 by medical-grade adhesive.

Figure 3:
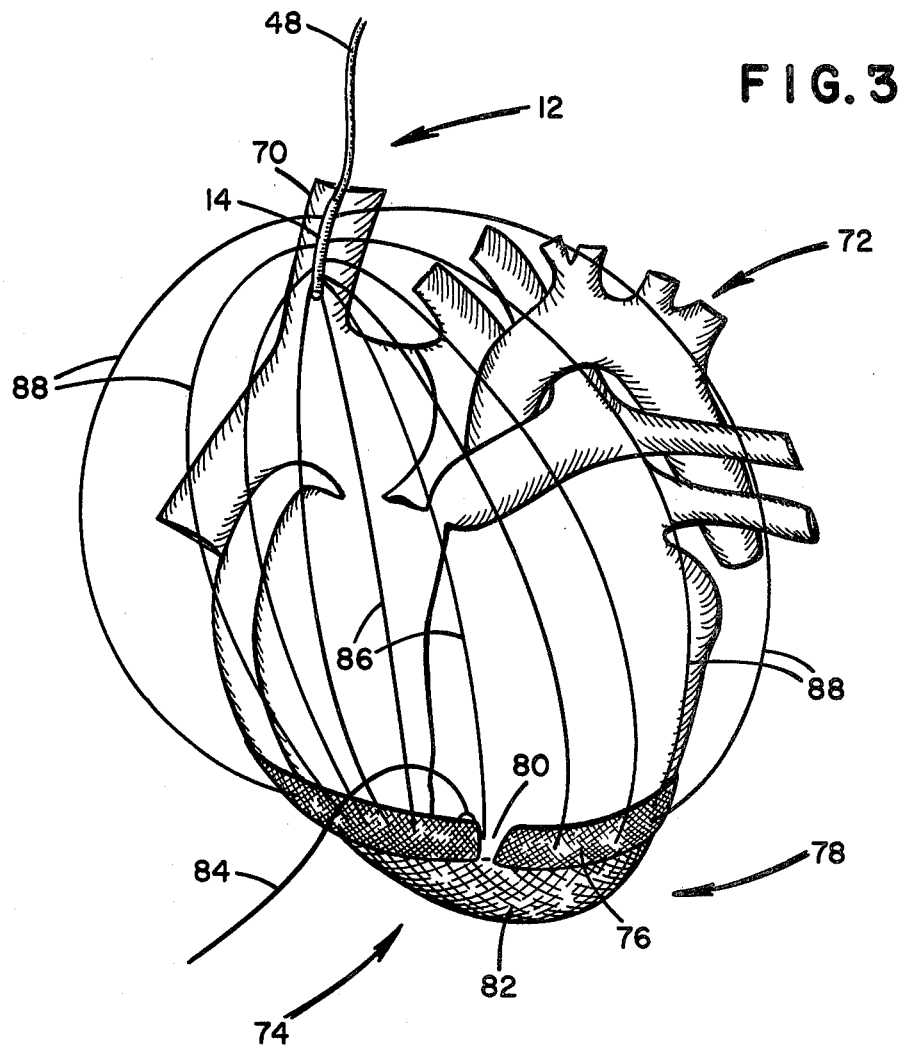
FIG. 3 is a schematic anterior view of a heart having a catheter electrode system of the present invention in the superior vena cava and acting against a conformal apex electrode.

With reference now to FIG. 3, the wound, spring wire electrode 14 of the inventive catheter electrode system 12 is shown positioned in the superior vena cava 70 of a heart 72. It should be understood, however, that the spring wire electrode 14 may be located in other positions in or about the heart, such as, for example, in the coronary sinus. The catheter electrode system 12 is introduced through a peripheral vein, such as the right jugular vein, by means of surgery similar to that involved in the implantation of a pacing catheter.

Also illustrated in FIG. 3 is an apex electrode 74 which comprises a band 76 of electrically conductive material which substantially surrounds the entire circumference of the apex 78. The band 76 is split at 80 so as to enable adaption to various apical forms. The surface of the apex electrode 74 facing away from the heart 72 is covered by an insulating material 82 which cups the entire apex of the heart. The surface of the apex electrode 74 facing the heart is conductive, and is in intimate contact with tissue. Electrical energy is delivered to the apex electrode through the means of a lead 84, which, as is illustrated, extends upwardly from the apex of the heart. This apex electrode 74, which may be positioned either within or outside the pericardium, is described in more detail in U.S. Pat. No. 4,030,509, the disclosure of which patent is expressly incorporated herein by reference.

When electrical energy is applied to the catheter electrode system 12 and the apex electrode 74, an electrical field is developed through the heart which is represented by field lines 86 and 88. The more central field lines 86 pass through the central regions of the heart, while the more remote field lines encompass the generally external surfaces of the ventricles. In this arrangement, more electrical energy flows through the myocardium than in prior art arrangements employing a bipolar catheter system.

It is contemplated that the cardioverting electrode set comprising the wound wire electrode 14 and the apex electrode 74 be capable of continually monitoring cardiac function and transmitting information to the implanted pulse generator 58. The pulse generator includes fibrillation detection circuitry, as well as circuitry of effecting the discharge of cardioverting energy through the heart. Accordingly, a fibrillating heart will be sensed by the implanted electrodes, the detector portion of the implanted pulse generator will diagnose fibrillation and will initiate the charging of a discharge capacitor, and when the capacitor is adequately charged, the pulse generator will effect the delivery of a cardioverting pulse to the electrodes. Such pulse generators, with detector stages, are well known. See, for example, commonly assigned U.S. Pat. No. Re27,652 and U.S. Application Ser. No. 620,025, filed on Sept. 30, 1975.

Above, specific embodiments of the present invention have been described. It should be appreciated, however, that these embodiments were described for purposes of illustration only, without any intention of limiting the scope of the present invention. Rather, it is the intention that the present invention be limited not by the above, but only as is defined in the appended claims.

What is claimed is:

1. A large surface area catheter electrode having a smooth outer surface and being of a uniform diameter throughout its discharge surface, for permanent implantation in a body and for cardioverting a malfunctioning heart, the electrode comprising:
   an electrically conductive resilient wire discharge electrode having an elongated coil wound section and proximal and distal ends said coil wound section being of a solid, single conductive material;
   an electrically conductive lead extending to said wound section of said resilient wire electrode and having proximal and distal ends, said proximal end being adapted for connection to a pulse generator;
   connector means for electrically connecting said lead to said resilient wire discharge electrode; and
   a filler material substantially filling said wound section of said resilient wire electrode so that only the outer periphery of said wound section is exposed to the body.

2. The catheter electrode of claim 1, in which said wound section of said resilient wire discharge electrode comprises essentially the entire length of said resilient wire electrode between said proximal and distal ends.

3. The catheter electrode of claim 1, in which the outer periphery of said wound section is ground and polished to have an essentially flat, smooth surface exposed to the body.

4. The catheter electrode of claim 1, wherein said lead is silver tinsel wire.

5. The catheter electrode of claim 1, wherein said lead is gold tinsel wire.

6. The catheter electrode of claim 1, wherein said filler material is electrically insulating.

7. The catheter electrode of claim 1, wherein said filler material is electrically conductive.

8. The catheter electrode of claim 1, and further comprising a protective tube means extending at least partially through said wound section of said resilient wire discharge electrode; and wherein said lead extends through said protective tube means.

9. The catheter electrode of claim 1, wherein said connector means comprise first and second connector sections; wherein said first connector section electrically connects the distal end of said lead to the distal end of said wound section; and wherein said second connector section defines a redundant connection between said lead and said wound section, at the proximal end of said wound section.

10. The catheter electrode of claim 1, wherein adjacent coils of said wound section are spaced from one another.

11. The catheter cathode of claim 1, wherein said wound section is of titanium.

12. A body implantable, large surface area cardioverting catheter electrode having a smooth outer surface and being of a uniform diameter throughout its discharge surface, the electrode comprising:
an elongated electrically conductive resilient wire discharge electrode having proximal and distal ends, said resilient wire electrode comprising a solid wire of a single conductive material, and being wound into the shape of a helical coil;
first electrical connector means electrically connected to the distal end of said resilient wire discharge electrode;
second electrical connector means electrically connected to the proximal end of said resilient wire discharge electrode;
an electrically conductive lead having a distal end electrically connected to said first and said second electrical connector means defining a redundant connection between said lead and said resilient wire electrode and having a proximal end adapted for connection to a source of electrical energy.

13. The catheter electrode of claim 12, and further comprising a filler material substantially filling said helical coil of said resilient wire discharge electrode so that only the outer periphery of said helical coil is exposed to the body.

14. The catheter electrode of claim 13, wherein said filler material is electrically conductive.

15. The catheter electrode of claim 12, wherein the exterior surface of said catheter electrode is substantially circular in cross section; and wherein said discharge electrode is formed from wound wire ground flat on its exterior surface its entire length.

16. The catheter electrode of claim 12, and further comprising a protective tube means surrounding said lead between said first and second electrical connector means.

17. The catheter electrode of claim 15, wherein said protective tube is electrically conductive.

18. The catheter electrode of claim 12, and further comprising an electrically insulating tube means connected to said second electrical connector means adjacent said proximal end of said resilent wire discharge electrode and extending toward the proximal end of said lead and surrounding said lead.

19. The catheter electrode of claim 12, wherein said lead is of silver tinsel wire.

20. The catheter electrode of claim 12, wherein said lead is of gold tinsel wire.

21. The catheter electrode of claim 12, wherein said discharge electrode is of titanium.

22. A large surface area cardioverting catheter electrode for implantation in a body, the electrode having a smooth outer surface, being of a uniform diameter throughout its discharge surface, and comprising:
an elongated electrically conductive solid spring wire of a single conductive material, having proximal and distal ends and being formed into a helical coil having spaced apart turns, the outer peripheral surface of said spring wire being ground flat, and said proximal and distal ends of said spring wire extending longitudinally of said helical coil;
first electrical connector means electrically connected to the distal end of said spring wire;
second electrical connector means electrically connected to the proximal end of said spring wire;
an electrically conductive lead connected to and extending past said second electrical connector means and connected to said first electrical connector means defining a redundant connection between said lead and said solid spring wire, and having a proximal end adapted for connection to a source of defibrillating electrical energy;
protective tube means surrounding said lead between said first and second electrical connector means;
an elastomeric spacer material filling said helical coil of said spring wire so that only the flat outer peripheral surface of said helical coil is exposed to the body; and
an electrically insulating elastomeric tube means extending from said second electrical connector means adjacent said proximal end of said spring wire and extending away from said proximal end thereof, said electrically insulating elastomeric tube means surrounding said lead.

23. The catheter electrode of claim 22, and further comprising a male plug at the proximal end of said lead and having prong means for connection to said source of cardioverting electrical energy.

24. A monopolar large surface area catheter cardioverting electrode having a smooth outer surface and being of a uniform diameter throughout its discharge surface, the electrode comprising:
an elongated discharge surface comprised of a solid conductive wire of a single conductive material and wound into a helical coil;
a lead having one end electrically connected to said conductive wire and having its opposite end provided with a connector for association with a pulse generator; and
filler means for maintaining the diameter of said helical coil and for defining said uniform electrode diameter.

25. The electrode of claim 24, wherein said lead is electrically connected to said conductive wire at at least two locations.

26. The electrode of claim 25, and further comprising first and second connectors for electrically connecting said lead to said conductive wire at two spaced-apart locations.

27. The electrode of claim 26, and further comprising a protective tube surrounding said lead between said first and second connectors.

28. The electrode of claim 25, wherein said discharge surface is on the order of 3 inches in length.

29. The electrode of claim 25, wherein said conductive wire is titanium; and wherein said lead is silver.

30. The electrode of claim 25, wherein said filler means is an insulating material.

31. The electrode of claim 25, wherein the coils of said discharge surface are spaced apart from adjacent coils.

32. The electrode of claim 25, wherein said filler means is a conductive material.

33. A large surface area monopolar cardioverting catheter electrode having a smooth outer surface and being of a uniform diameter throughout its discharge surface, the electrode comprising:
an elongated, spiral wound electrically conductive discharge surface of a single conductive material;

a lead having one end electrically connected at first and second locations to said discharge surface, and having opposite ends provided with a connector for association with a pulse generator;

first and second connector means electrically connected to respective opposite ends of said discharge surface and to said lead at said first and second locations defining a redundant connection between said lead and said discharge surface; and protector means surrounding said lead between said first and second locations.

34. The electrode of claim 33, wherein said protector means is a tube having an internal diameter in excess of the external diameter of said lead.

35. The electrode of claim 34, wherein said tube is of an insulating material.

36. The electrode of claim 34, wherein the internal diameter of said discharge surface is in excess of the external diameter of said tube; and further comprising a filler material intermediate said discharge surface and said tube for maintaining the spacing therebetween.

* * * * *